United States Patent [19]

Schiffert

[11] 4,302,678
[45] Nov. 24, 1981

[54] FLUORESCENT STANDARD FOR SCANNING DEVICES

[75] Inventor: Phillip W. Schiffert, Oak Park, Ill.

[73] Assignee: Magnaflux Corporation, Chicago, Ill.

[21] Appl. No.: 115,510

[22] Filed: Jan. 25, 1980

[51] Int. Cl.³ ............... G01N 21/38; G01D 18/00; G09K 3/00
[52] U.S. Cl. ............... 250/461 R; 250/252; 250/302; 250/522
[58] Field of Search ........... 250/252, 302, 483, 461 R, 250/484, 522, 474, 493, 485; 252/301.1 L

[56] References Cited

U.S. PATENT DOCUMENTS 3,225,242  12/1965  Regelson ............... 250/493
3,889,124  6/1975  Yamamoto et al. ............... 250/462

FOREIGN PATENT DOCUMENTS 2327554  5/1977  France ............... 250/484

OTHER PUBLICATIONS

Garbe, "Glass Fluorescence Standard", Research Disclosure, May 1976, p. 36.
Schmidt, "A New Method for Measuring Fluorescent Brightness and Color", Materials Evaluation, 12-66, pp. 697–702.

Primary Examiner—Davis L. Willis
Assistant Examiner—Carolyn E. Fields
Attorney, Agent, or Firm—Hill, Van Santen, Steadman, Chiara & Simpson

[57] ABSTRACT

A standard specimen for calibrating an ultraviolet scanning system of the type used to detect surface flaws in workpieces by penetrant testing including a piece of glass which has the characteristic of emitting fluorescent radiation upon excitation by ultraviolet light, and a heat conductive carrier element rigidly supporting the piece of glass therein. The standard specimen provides a means for confirming instrumentation stability despite changes in temperature.

1 Claim, 4 Drawing Figures

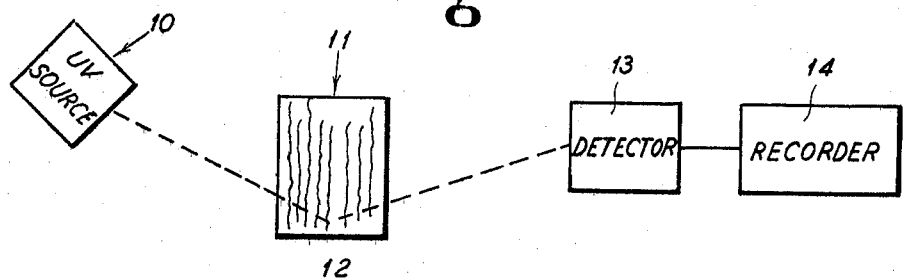
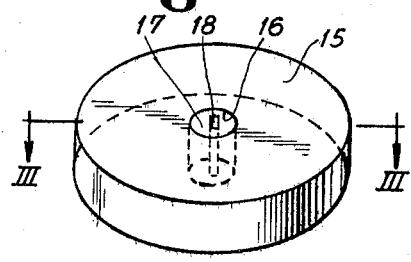
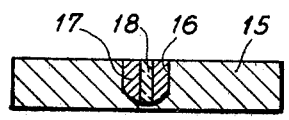
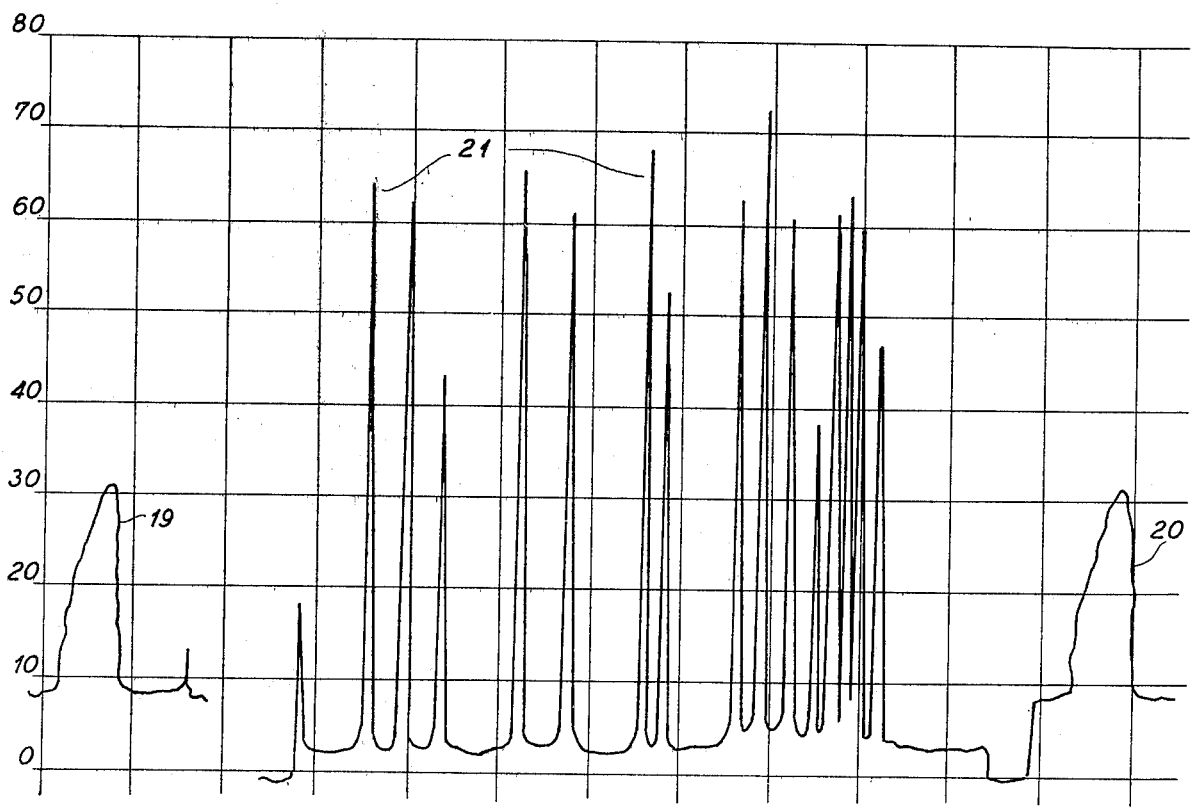

FLUORESCENT STANDARD FOR SCANNING DEVICES

BACKGROUND OF THE INVENTION

1. Field of the Invention

This invention is in the field of testing devices, and is particularly concerned with a specimen which can be used to confirm stability of instrumentation used for ultraviolet scanning of test pieces in a non-destructive penetrant inspection process.

2. Description of the Prior Art

The penetrant method for determining surface discontinuities, utilizing a fluorescent penetrant material is being widely used in industry. Basically, the process consists in first cleaning the surface of the piece and then flooding it with a penetrant composition containing a fluorescent dye. The penetrant is permitted to dwell on the surface of the piece until the penetrant can become lodged within surface flaws. The excess penetrant is then wiped off or otherwise removed, leaving only the penetrant deposits which have found their way into surface and subsurface defects. Then, a wet or dry developer is applied to the piece to aid in extracting the entrapped penetrant from the flaws and making it more readily visible against the surface of the workpiece. The inspection of the piece for locating the flaws and determining the relative magnitude is normally done by an operator working in an inspection booth illuminated with ultraviolet or black light.

In more recent times, the fluorescent penetrant type inspection process has become more sophisticated with the introduction of scanning devices which direct ultraviolet light at the surface of a workpiece to be inspected, and a detector sensitive to fluorescent indications transforms the light impulses into electrical impulses which operate a recorder or the like. In order to provide meaningful results, however, this type of scanning equipment must be periodically calibrated against a suitable standard. There have been numerous such standards developed over the years, in most cases including a relatively thin steel plate which is coated with a thin, brittle layer of chromium plating. The plate is then bent around an arcuate surface to develop a series of fine cracks which can be detected by the fluorescent penetrant inspection process. Originally it was thought that such cracked plates could themselves be standards for calibrating the scanning equipment inasmuch as the location, length and depth of the cracks remain the same, but this has not proven to be the case. It was found, for example, that a given plate when tested by fluorescent penetrants would consistently give the same pattern of flaw indications but of substantially different intensities. In view of this fact, it is not possible to use cracked plates themselves as primary standards. The need still exists, therefore, for a standard which can simultaneously confirm the stability of the ultraviolet light level in the scanner, and the operation of the detector. Such a standard could be scanned before or after a test panel to provide confirmation of the validity of comparisons with previously run data. With a suitable primary standard, recorder deflection produced by the standard could be varied by adjustment in the distance of the ultraviolet light source or by varying the high voltage on the photo multiplier tube, should instrumentation shift be observed. The provision of a primary standard which accomplishes these purposes is the principal object of the present invention.

SUMMARY OF THE INVENTION

The present invention provides a primary standard for calibrating an ultraviolet scanning system utilizing a piece of glass having the characteristics of emitting fluorescent radiation upon excitation by ultraviolet light, the piece of glass being received within a heat conductive carrier element rigidly supporting the piece of glass therein. In a preferred form of the invention, the carrier element and the glass present planar surfaces to incident ultraviolet radiation. In the currently preferred form of the invention, the specimen is embedded in a sheath of lead or low melting alloy which in turn is received in a relatively large disk composed of a good heat conductive material such as copper or brass.

BRIEF DESCRIPTION OF THE DRAWINGS

The present invention is more completely described in conjunction with the attached sheet of drawings in which:

FIG. 1 is a schematic view of an ultraviolet scanning system in its entirety;

FIG. 2 is a view in perspective of a fluorescent standard produced according to the present invention; FIG. 3 is a cross-sectional view taken substantially along the line III—III of FIG. 2; and FIG. 4 is a typical recorder chart illustrating the manner in which the present invention may be used.

DESCRIPTION OF THE PREFERRED EMBODIMENTS

In FIG. 1, reference numeral 10 indicates generally a scanning type ultraviolet source which directs a beam of ultraviolet light at a test piece 11 which may consist, for example, of a steel plate having a brittle chromium plated surface in which there are finely divided cracks 12. The fluorescence caused by the entrapped penetrant being irradiated by the ultraviolet beam actuates a detector 13 to change the light variations into electrical variations, which variations can then be recorded on a suitable recorder 14.

In FIG. 2, there is illustrated a specimen according to the present invention in a preferred geometric form. There is shown a disk 15 composed of a good heat conductive material such as copper or brass, the disk 15 having a central bore 16 therein. Located within the bore 16 is a sheath 17 of lead or similar low melting, heat conductive material. The sheath 17 positions a piece of glass 18 centrally within the bore 16. A suitable adhesive such as an epoxy adhesive can also be used to orient the glass relative 18 to the disk 15.

The glass 18 consists of a glass composition which has the characteristic of fluorescing, that is, emitting fluorescent radiation upon excitation by ultraviolet light. One such material is marketed by Corning Glass Works, as their glass No. 3750. It has a coefficient of expansion of $8.0 \times 10^{-7}$ inch/inch/° C. in the range of 0° to 300° C. It is believed to be a yellow, uranium oxide containing potassium borosilicate glass. Other products which have the property of fluorescing under ultraviolet radiation are Corning glasses Nos. 3780 and 3718.

The combination of the fluorescent glass specimen in the relatively massive heat conductive disk serves to efficiently remove heat away from the glass during extended irradiation by the ultraviolet source. The brass or copper has sufficient mass in the surface so that the temperature of the glass does not appreciably increase over extended periods of illumination. In effect, therefore, the disk forms a heat sink for the more temperature sensitive glass specimen.

A reference line may be scribed from the edges of the glass to opposite edges of the disk for scanning alignment and the top of the disk may be marked to insure repeatable scanning values.

A typical scan record utilizing the standard of the present invention is illustrated in FIG. 4 of the drawings. To the left and to the extreme right are a pair of scan tracings 19 and 20 which were taken before and after scanning of a standard cracked panel to produce a series of pulses 21 denoting fluorescent response. Since the response of the standard does not vary with time or temperature, this response can be used to confirm instrumentation stability between tests of workpieces. The standard simultaneously confirms the stability of the ultraviolet light level and of the detector. The recorder deflection produced by the standard can be varied by adjustment in the distance of the ultraviolet light source or by varying the high voltage on the photo multiplier tube, if instrumentation shift is observed.

It should be evident that various modifications can be made to the described embodiments without departing from the scope of the present invention.

I claim as my invention:

1. A standard specimen for calibrating an ultraviolet scanning system comprising:

a piece of borosilicate glass containing uranium oxide and having the characteristic of emitting fluorescent radiation upon excitation by ultraviolet light, and a heat conductive carrier element rigidly supporting and encasing said piece of glass therein while leaving at least one surface of said glass exposed to ultraviolet radiation, said one surface being flush with a planar surface of said carrier element into which it extends.

* * * * *